(12) United States Patent
Henriksen et al.

(10) Patent No.: US 8,846,361 B2
(45) Date of Patent: *Sep. 30, 2014

(54) SOLID PHYTASE COMPOSITIONS STABILIZED WITH CORN STEEP LIQUOR

(75) Inventors: Lotte Rugholm Henriksen, Vanlose (DK); Erik Marcussen, Ballerup (DK)

(73) Assignee: Novozymes A/S, Bagsvaerd (DK)

( * ) Notice: Subject to any disclaimer, the term of this patent is extended or adjusted under 35 U.S.C. 154(b) by 164 days.

This patent is subject to a terminal disclaimer.

(21) Appl. No.: 12/403,412

(22) Filed: Mar. 13, 2009

(65) Prior Publication Data

US 2009/0169681 A1 Jul. 2, 2009

Related U.S. Application Data

(63) Continuation of application No. 10/618,477, filed on Jul. 11, 2003, now abandoned, which is a continuation of application No. 09/410,503, filed on Oct. 1, 1999, now Pat. No. 6,610,519.

(60) Provisional application No. 60/103,522, filed on Oct. 8, 1998.

(30) Foreign Application Priority Data

Oct. 2, 1998 (DK) .................................. 1998 01251

(51) Int. Cl.
| | |
|---|---|
| C12N 9/96 | (2006.01) |
| C12N 9/98 | (2006.01) |
| A61K 38/46 | (2006.01) |
| A23K 1/165 | (2006.01) |
| C12N 11/02 | (2006.01) |
| C12N 9/14 | (2006.01) |
| C12N 9/16 | (2006.01) |

(52) U.S. Cl.
CPC .. *C12N 9/98* (2013.01); *C12N 9/96* (2013.01); *C12N 9/16* (2013.01); *Y10S 426/807* (2013.01)

USPC ........... 435/188; 424/94.6; 424/442; 426/61; 426/807; 435/177; 435/187; 435/195

(58) Field of Classification Search
None
See application file for complete search history.

(56) References Cited

U.S. PATENT DOCUMENTS

| | | | |
|---|---|---|---|
| 4,106,991 A | | 8/1978 | Markussen et al. |
| 4,859,485 A | | 8/1989 | Linton et al. |
| 5,750,005 A | | 5/1998 | Akhtar |
| 5,876,992 A | * | 3/1999 | De Rosier et al. ............ 435/188 |
| 5,972,669 A | | 10/1999 | Harz et al. |
| 5,989,600 A | * | 11/1999 | Nielsen et al. ................. 426/52 |
| 6,060,298 A | | 5/2000 | Lassen et al. |
| 6,136,772 A | | 10/2000 | De Lima et al. |

FOREIGN PATENT DOCUMENTS

| | | |
|---|---|---|
| EP | 0 758 018 | 2/1997 |
| EP | 0 897 010 | 2/1999 |
| EP | 0 897 985 | 2/1999 |
| WO | WO 93/16175 | 8/1993 |
| WO | WO 97/39116 | 10/1997 |
| WO | WO 98/28408 | 7/1998 |

OTHER PUBLICATIONS

Rutgersson et al., Cereal Chemistry, vol. 74, No. 6, pp. 727-732 (1997).

* cited by examiner

*Primary Examiner* — David M Naff
(74) *Attorney, Agent, or Firm* — Kelly R. Reynolds

(57) ABSTRACT

The present invention relates to solid enzyme, in particular phytase, compositions stabilized with a lactic acid source such as Corn Steep Liquor (CSL), and methods of producing the same. Preferred compositions additionally comprise starch and disaccharides such as lactose or trehalose.

22 Claims, No Drawings

SOLID PHYTASE COMPOSITIONS STABILIZED WITH CORN STEEP LIQUOR

CROSS-REFERENCE TO RELATED APPLICATIONS

This application is a continuation of Ser. No. 10/618,477 filed on Jul. 11, 2003, now abandoned, which is a continuation of U.S. application Ser. No. 09/410,503 filed Oct. 1, 1999 now U.S. Pat. No. 6,610,519, which issued as U.S. Pat. No. 6,610,519, which claims priority or the benefit under 35 U.S.C. 119 of Danish application no. PA 1998 01251 filed on Oct. 2, 1998 and U.S. provisional application No. 60/103,522 filed on Oct. 8, 1998, the contents of which are fully incorporated by reference.

BACKGROUND OF THE INVENTION

1. Field of the Invention

The present invention relates to solid phytase compositions which have been stabilized with a lactic acid source such as Corn Steep Liquor (CSL), and methods of producing the same.

2. Description of Related Art

The addition of phytase to animal feed to eliminate the anti-nutritional effects of phytic acid is well described, see, e.g., WO 98/28408 and WO 98/28409.

The stabilization of liquid phytase formulations with urea, glycerol or sorbitol is disclosed in WO 93/16175.

Salt-stabilized solid phytase compositions are disclosed in EP 0 758 018 A1.

Plant seeds, cereal grains and legumes are usual components of animal feed. Some of those seeds contain phytic acid, and often also endogenous phytase enzymes.

According to investigations performed by the applicant, endogenous phytase activity in animal feed is at a very low level of around 0.5 units/g.

According to e.g., the two above first-cited WO-references, when supplementary phytase has been added to feed, the phytase activity in the feed is in the range of 0.01-20 units/g.

SUMMARY OF THE INVENTION

The present invention relates to solid phytase compositions which comprise (a) an enzyme having phytase activity; and (b) a lactic acid source, wherein the phytase activity of the composition is above 20 units/g.

DETAILED DESCRIPTION OF THE INVENTION

In the present context, the expression "enzyme (or polypeptide) having phytase activity" or "phytase" includes any enzyme capable of effecting the liberation of inorganic phosphate from phytic acid or from any salt thereof (phytates).

Phytic acid is myo-inositol 1,2,3,4,5,6-hexakis dihydrogen phosphate (or for short myo-inositol hexakisphosphate). In what follows, unless otherwise indicated, the terms "phytic acid" and "phytate," are used synonymously or at random.

In the present context, the term "units" means units of enzyme, in particular phytase, activity. Any method for determining phytase activity can be used.

In a preferred embodiment, one unit of phytase activity is defined as the amount of enzyme that liberates 1 micro mole inorganic ortho-phosphate per min. under the following conditions: A pH which is within the range of +/−1 pH unit from the optimum pH of the actual enzyme; a temperature which is within the range of +/−20° C. from the optimum temperature of the actual enzyme; using as a substrate phytic acid or any salt thereof in a suitable concentration.

Preferably, the substrate is dodeca-sodium phytate in a concentration of 0.005 mole/l.

Preferably, the pH is within the range of +/−0.5 pH unit from the optimum pH; more preferably the pH is the optimum pH.

Preferably, the temperature is within the range of +/−10° C. from the optimum temperature; more preferably the temperature is the optimum temperature.

Preferably, the optimum pH and optimum temperature refers to the use of sodium phytate as a substrate.

In another preferred embodiment, the phytase activity is determined in the unit of FYT, one FYT being the amount of enzyme that liberates 1 micro mole inorganic ortho-phosphate per min. under the following conditions: pH 5.5; temperature 37° C.; substrate: sodium phytate ($C_6H_6O_{24}P_6Na_{12}$) in a concentration of 0.0050 mole/l.

In a further preferred embodiment, the phytase activity is measured using the FTU assay.

The FYT- and FTU-assays are described in more detail in the experimental part.

In preferred embodiments, the phytase activity of the solid composition of the invention is above 25, 50, 100, 250, 500, 750 or even above 1000 units/g.

Optionally, the phytase activity of the solid composition is below 100,000 units/g, more preferably below 75,000 units/g, even more preferably below 50,000 units/g, or below 40,000 units/g, or below 25,000 units/g, or even below 10,000 units/g, mostly preferred below 5,000 units/g.

Preferred ranges of phytase activity are 25-100,000, 25-75,000, 35-50,000, or 50-40,000 units/g; more preferably 100-25.000 units/g; even more preferably 500-10.000 units/g; mostly preferred 1000-5000 units/g.

In the present context, any enzyme having phytase activity can be used.

Phytases have been derived from plants as well as from microorganisms. Amongst the microorganisms, phytase producing bacteria as well as phytase producing fungi are known. From the plant kingdom, e.g., a wheat-bran phytase is known (Thomlinson et al., 1962, *Biochemistry* 1: 166-171). An alkaline phytase from lilly pollen has been described by Barrientos et al., 1994, *Plant. Physiol.* 106: 1489-1495.

Amongst the bacteria, phytases have been described which are derived from *Bacillus subtilis* (Paver and Jagannathan, 1982, *Journal of Bacteriology* 151: 1102-1108) and *Pseudomonas* (Cosgrove, 1970, *Australian Journal of Biological Sciences* 23: 1207-1220). Still further, a phytase from *E. coli* has been purified and characterized by Greiner et al., 1993, *Arch. Biochem. Biophys.* 303:107-113).

Phytase producing yeasts are also described, such as *Saccharomyces cerevisiae* (Nayini et al., 1984, *Lebensmittel Wissenschaft und Technologie* 17: 24-26. However, this enzyme is probably a myo-inositol monophosphatase (Wodzinski et al., *Adv. Appl. Microbiol.* 42: 263-303). AU-A-24840/95 describes the cloning and expression of a phytase of the yeast *Schwanniomyces occidentalis*.

There are several descriptions of phytase producing filamentous fungi, primarily belonging to the fungal phylum of Ascomycota (ascomycetes). In particular, there are several references to phytase producing ascomycetes of the *Aspergillus* genus such as *Aspergillus terreus* (Yamada et al., 1986, *Agric. Biol. Chem.* 322: 1275-1282). Also, the cloning and expression of the phytase gene from *Aspergillus niger* var. *awamori* has been described (Piddington et al., 1993, *Gene* 133: 55-62). EP 0 420 358 describes the cloning and expression of a phytase of *Aspergillus ficuum* (*niger*). EP 0 684 313 describes the cloning and expression of phytases of the ascomycetes *Myceliophthora thermophila* and *Aspergillus terreus*.

Phytases derived from fungi of the phylum Basidiomycota are disclosed in WO 98/28409 and WO 98/28408.

Modified phytases or phytase variants are obtainable by methods known in the art, in particular by the methods disclosed in EP 0897010, EP 0897985, PCT/DK99/00153 and PCT/DK99/00154. The phytases disclosed in these four patent applications can also be used in the compositions of the present invention.

A solid or dry composition is a particulate material comprising, preferably consisting essentially of, or consisting of, freely flowing particles of a size ranging from (micro-m) 0.01, or from 1.0, or preferably from around 1 to 1000, or to 1200, or to 1500, or even up to 2000 (micro-m).

Preferably, a solid or dry phytase composition is such composition which can be prepared from liquid phytase concentrates e.g., by spray drying, spray cooling (prilling), or any type of granulation.

For spray drying, no further components need to be added to the liquid phytase concentrate.

For spray cooling, a meltable component—such as palm oil (and/or another meltable vegetable oil or fat), hydrogenated palm oil (and/or another hydrogenated vegetable oil), tallow, hydrogenated tallow or a wax functions as a matrix. The phytase and other ingredients, if any, are introduced into the melted, meltable component, and the melt is then allowed to solidify under particle-forming conditions, typically in a spray drying tower.

For many uses, however, including the use in animal feed, granulates are usually preferred for a number of reasons. One reason is that they may readily be mixed with feed components, or more preferably, form a component of a pre-mix which contains other desired feed additives such as vitamins and minerals.

The particle size of the enzyme granulates preferably is compatible with that of the other components of the mixture. This provides a safe and convenient mean of incorporating enzymes into, e.g., animal feed.

The size of a particle may be regarded as the greatest linear dimension of the particle; thus, in the case of, e.g., a substantially spherical particle (such as a substantially spherical granulate particle), the particle size in question will be the diameter of the particle.

Agglomeration granulates and agglomerated powders may be prepared using agglomeration technique in a high shear mixer (e.g., Lödige) during which one or more filler materials and the enzyme are co-agglomerated to form granules.

Absorption granulates are prepared by having cores of one or more carrier materials to absorb/be coated by the enzyme.

Typical filler materials are salts such as di-sodium sulphate and calcium-lignosulphonate. Other fillers are silica, gypsum, kaolin, talc, magnesium aluminium silicate and cellulose fibers. Optionally, binders such as dextrins are also included in agglomeration granulates.

Typical carrier materials may consist of particulate cores having a suitable particle size. The carrier may be water soluble or water insoluble, e.g., starch, e.g., in the form of cassava or wheat; or a sugar (such as sucrose or lactose), or a salt (such as sodium chloride or sodium sulphate).

Optionally, the granulates are coated with a coating mixture. Such mixture comprises coating agents, preferably hydrophobic coating agents, such as hydrogenated palm oil and beef tallow, and if desired other additives, such as calcium carbonate or kaolin.

WO 97/39116 discloses preferred processes for making solid compositions of the invention in the form of enzyme-containing granules or an enzyme-containing granulate, see in particular the sections of the detailed description therein headed cores, binders, fillers, plasticizers, fibrous materials, superabsorbents, coating layers, enzymes, other adjunct ingredients (these sections being hereby incorporated by reference herein). However, WO 97/39116 does not disclose the inclusion in the solid composition of a lactic acid source.

Preferred methods of preparing phytase granulates are referred to in Example 3.

Preferred solid compositions of the invention are enzyme compositions. The preferred compositions are concentrated, viz. of an activity of above 20 units/g. Thus, the concept of solid enzyme composition comprises in particular, but are not limited to, spray-dried enzyme preparations, enzyme granulates, e.g., agglomeration granulates and absorption granulates, coated as well as un-coated, and enzyme-containing pre-mixes for animal feed. Phytase is a preferred enzyme.

Liquid enzyme (phytase) concentrates can e.g., be prepared as follows: The enzyme source, typically a phytase-containing fermentation broth, is subjected to a primary separation step (e.g., using a decanter, a centrifuge, or a filter press), followed by a second polish filtration and/or germ filtration step. Finally the liquid is concentrated, e.g., using ultra filtration, followed by a germ filtration. A typical dry matter content is in the range of 10-30%, preferably 15-25%, more preferably 17-22%.

In the present context, "a" generally means "one or more" or "at least one." This applies, inter alia, for the following mandatory or optional components of the compositions of the invention: Phytase, lactic acid source, CSL, starch, disaccharide, filler, and carrier.

Unless otherwise indicated, all percentage indications are weight/weight, by reference to dry matter content. Preferably, "units/g" also refers to dry matter content. Dry matter content can be determined by any method known in the art, such as refractometer or drying in an oven to release humidity.

Unless otherwise indicated, the expression "above" generally means "≥", whereas the expressions "up to" or "below" mean "≤".

In the present context a "lactic acid source" or a "lactic acid preparation" is any composition which comprises the compound lactic acid or any lactates, i.e., any salts thereof (lactic acid is 2-hydroxy propanic acid). Likewise, "lactic acid" as used herein includes any lactates. These expressions are used interchangeably for the lactic acid source, resp. the lactic acid, as is, and for the dry matter part thereof.

A non-limiting list of lactic acid sources is the following: Lactic acid and lactates as relatively pure chemical compounds (purity of, say, above 70%, 80%, 90%); lactic acid and lactates as more impure substances (purity of, say, above 5%, 10%, 15%, 20%, 25%, 30%, 40%, 50%); any natural or synthetical composition which comprises lactic acid in an amount of above 5%, preferably above 10%, 15%, 20%, 25%, 30%, 40%, 50%, 70%, 80%, 90%.

The solid enzyme compositions of the invention preferably comprise up to 20, preferably up to 15, more preferably up to 10, still more preferably up to 9, 8, 7, 6, 5, 4, 3, 2, 1, 0.75 or 0.5% lactic acid. The content of lactic acid is preferably above 0.001, preferably above 0.002, 0.004, 0.006, 0.008, 0.01, 0.02, 0.04, 0.06, 0.08, 0.1, 0.12, 0.14, 0.16, 0.18, 0.2, 0.22, 0.24, 0.26, 0.28, or above 0.3%. Preferred ranges of content of lactic acid are 0.01-10%, 0.02-9%, 0.03-8%, 0.04-7%, 0.05-6%, 0.06-7%, 0.07-6%, 0.08-5%, 0.09-4%, or 0.1-3%.

Any assay for lactic acid can be used. Preferred lactic acid assays are from SIGMA: (1) Assay kit catalogue no. 735-10 (enzymatical assay, lactate degraded to pyruvate and hydrogen peroxide in the presence of oxidase); or (2) Assay kit catalogue no. 826-A and 826-B (ultraviolet, endpoint, lactate converted into pyruvic acid in the presence of lactate dehydrogenase and NAD).

A preferred lactic acid source is Corn Steep Liquor or CSL. CSL is a commercially available product, see for instance Merck Index, 1996, 4$^{th}$ edition, Index no. 2598. It is a viscous yellowish or dense brown liquid obtained by concentration of corn steep water. The dry matter content is usually 45-55%, preferably 48-52%. The pH is in the range of 3-5, preferably 3.5-4.5. The protein content (Dry Matter) is typically 30-50%, preferably 35-45%. The acidity (as lactic acid) is typically 10-30% (Dry Matter), preferably 12-25%.

"CSL" as used herein refers to the product as such, or to its dry matter part.

In a preferred embodiment, the solid composition of the invention comprises 0.01-15%, preferably 0.1-10%, more preferably 1-5% of CSL.

For analyzing CSL-content, any method can be used. A preferred HPLC method for fingerprinting and quantifying CSL is indicated in Example 8. Another preferred method is Head Space Gas Chromatograph (HS-GC), preferably combined with mass spectrometry (MS).

In a preferred embodiment, the solid composition of the invention additionally comprises a starch source, typically in an amount of 0.1-20%, more preferably 0.2-10%, still more preferably 1-5%.

The concept of a starch source includes any natural or synthetic polysaccharides comprising glucose units interconnected by alpha-1,4 or alpha-1,6-linkages. Purity is preferably above 10, 20, 30, 40, 50, 60, 70, 80, 90, or 100%. A preferred starch source is Wheat Starch, which is a commercially available product. The expression "starch source" includes the starches and modified starches described in the section headed "Cores" of WO 97/39116, cited above.

In another preferred embodiment, the solid composition of the invention additionally comprises a disaccharide, preferably in an amount of 0.01-15%, even more preferred 0.1-10%, even more preferably 1-5%.

The concept of disaccharides includes any natural or synthetic disaccharides, whatever the monomers, and whatever the linkage type. Examples of such disaccharides are maltose, lactose, cellobiose, sucrose, and trehalose (non-limiting list). Preferably, the disaccharides are of a purity of above 10, 20, 30, 40, 50, 60, 70, 80 or even 90%. Preferred disaccharides are lactose and trehalose (alpha-D-glucose alpha-D-glucopyranoside, alpha-1,1 linkage).

In the process of the invention, all steps, e.g., those indicated in claim 14, can be performed simultaneously or sequentially. For example, steps (i) and (ii) sequentially or preferably simultaneously (mixing the lactic acid source and the phytase before spraying it onto the carrier); steps (iii) and (iv) simultaneously or sequentially, preferably simultaneously, in the same apparatus; applies also to "together with" of claim 12.

Further preferred embodiments of the invention are the following:

A solid composition which comprises at least one enzyme having phytase activity, and Corn Steep Liquor (CSL), wherein the phytase activity of the composition is in the range of 20-50.000 units/g. A preferred amount of CSL is within the range of 0.01-15% (dry matter content and w/w). Preferably, the composition additionally comprises Wheat Starch (WS), preferably in an amount within the range of 0.01-20% (dry matter content and w/w);

A process for preparing a granulate composition having a phytase activity in the range of 20-50.000 units/g, which method comprises the steps of (i) spraying a liquid phytase concentrate onto a carrier; (ii) spraying CSL onto the carrier; (iii) mixing; and (iv) drying;

A process for preparing a spray dried solid composition having a phytase activity in the range of 20-50.000 units/g, which method comprises the step of adding CSL to a liquid phytase concentrate before spray drying it.

The activities of the solid phytase compositions prepared in the present examples are in the range of 1000-3000 FTU/g before storage.

Example 1

FYT Assay 10 microliters diluted enzyme samples (diluted in 0.1 M sodium acetate, 0.01% Tween 20, pH 5.5) are added into 250 microliters 5 mM sodium phytate (Sigma) in 0.1 M sodium acetate, 0.01% Tween 20, pH 5.5 (pH adjusted after dissolving the sodium phytate; the substrate is preheated) and incubated for 30 minutes at 37° C. The reaction is stopped by adding 250 microliters 10% TCA and free phosphate is measured by adding 500 microliters 7.3 g FeSO4 in 100 ml molybdate reagent (2.5 g $(NH_4)_6Mo_7O_{24}.4H_2O$ in 8 ml $H_2SO_4$ diluted to 250 ml). The absorbance at 750 nm is measured on 200 microliter samples in 96 well microtiter plates. Substrate and enzyme blanks are included. A phosphate standard curve is also included (0-2 mM phosphate). 1 FYT equals the amount of enzyme that releases 1 micromol phosphate/min at the given conditions.

FTU Assay

One FTU is defined as the amount of enzyme, which at standard conditions (37° C., pH 5.5; reaction time 60 minutes and start concentration of phytic acid 5 mM) releases phosphate equivalent to 1 micromol phosphate per minute.

1 FTU=1 FYT

The FTU assay is preferred for phytase activity measurements on animal feed premixes and the like complex compositions.

Reagents/Substrates

Extraction Buffer for Feed Etc.

This buffer is also used for preparation of $PO_4$-standards and further dilution of premix samples.

0.22 M Acetate Buffer with Tween 20 pH 5.5

30 g sodium acetate trihydrate (MW=136.08 g/mol) e.g., Merck Art 46267 per liter and 0.1 g Tween 20, e.g., Merck Art 22184 pr. liter are weighed out.

The sodium acetate is dissolved in demineralized water.

Tween 20 is added, and the pH is adjusted to 5.50±0.05 with acetic acid.

Add demineralized water to total volume.

Extraction Buffer for Premix 0.22 M acetate buffer with Tween 20, EDTA, $PO_4^{3-}$ and BSA.

30 g sodium acetate trihydrate e.g., Merck Art 6267 per liter.

0.1 g Tween 20 e.g., Merck Art 22184 per liter.

30 g EDTA f.eks. Merck Art 8418 per liter.

20 g $Na_2HPO_4$, $2H_2O$ e.g., Merck Art 6580 per liter.

0.5 g BSA (Bovine Serum Albumine, e.g., Sigma Art A-9647 per liter.

The ingredients are dissolved in demineralized water, and pH is adjusted to 5.50±0.05 with acetic acid.

Add demineralized water to total volume.

BSA is not stable, and must therefore be added the same day the buffer is used.

50 mM $PO_4^{3-}$ Stock Solution 0.681 g $KH_2PO_4$ (MW=136.09 g/mol) e.g., Merck Art 4873 is weighed out and dissolved in 100 ml 0.22 M sodium acetate with Tween, pH 5.5.

Storage stability: 1 week in refrigerator.

0.22 M Acetate Buffer pH 5.5 without Tween

This buffer is used for production of phytic acid substrate).

150 g sodium acetate trihydrate (MW=136.08) e.g., Merck Art 6267 is weighed out and dissolved in demineralized water, and pH is adjusted with acetic acid to 5.50±0.05.

Add demineralized water to 5000 ml.

Storage stability: 1 week at room temperature.

Phytic Acid Substrate; 5 mM Phytic Acid

The volume of phytic acid is calculated with allowance for the water content of the used batch.

If the water content is e.g., 8.4% the following is obtained:

$$(0.005 \text{ mol/l} \times 923.8 \text{ g/mol})/(1/0.084)=5.04 \text{ g/l}$$

Phytic acid (Na-salt) (MW=923.8 g/mol) e.g., Sigma P-8810 is weighed out and dissolved in 0.22 M acetate buffer (without Tween). Addition of (diluted) acetic acid increases the dissolution speed.

The pH is adjusted to 5.50±0.05 with acetic acid.

Add 0.22 M acetate buffer to total volume.

21.7% Nitric Acid Solution

For stop solution.

1 part concentrated (65%) nitric acid is mixed into 2 parts demineralized water.

Molybdate Reagent

For stop solution.

100 g ammonium heptamolybdate tetrahydrate $(NH_4)_6Mo_7O_{24}, 4H_2O$, e.g., Merck Art 1182 is dissolved in demineralized water. 10 ml 25% $NH_3$ is added.

Add demineralized water to 1 liter.

0.24% Ammonium Vanadate

Bought from Bie & Berntsen.

Molybdate/Vanadate Stop Solution 1 part vanadate solution (0.24% ammonium vanadate)+1 part molybdate solution are mixed. 2 parts 21.7% nitric acid solution are added.

The solution is prepared not more than 2 hours before use, and the bottle is wrapped in tin foil.

Samples

Frozen samples are defrosted in a refrigerator overnight.

Sample size for feed samples: At least 70 g, preferably 100 g.

Feed Samples

Choose a solution volume which allows addition of buffer corresponding to 10 times the sample weight, e.g., 100 g is dissolved in 1000 ml 0.22 M acetate buffer with Tween, see enclosure 1. Round up to nearest solution volume.

If the sample size is approx. 100 g all the sample is ground in a coffee grinder and subsequently placed in tared beakers. The sample weight is noted. It is not necessary to grind not-pelleted samples. If a sample is too big to handle, it is sample split into parts of approx. 100 g.

Magnets are placed in the beakers and 0.22 M acetate buffer with Tween is added.

The samples are extracted for 90 minutes.

After extraction the samples rest for 30 minutes to allow for the feed to sediment. A 5 ml sample is withdrawn with a pipette. The sample is taken 2-5 cm under the surface of the solution and placed in a centrifuge glass, which is covered by a lid.

The samples are centrifuged for 10 minutes at 4000 rpm.

Premix Samples

Choose a solution volume which allows addition of buffer corresponding to 10 times the sample weight. Round up to nearest solution volume.

If the samples have been weighed (50-100 g) all of the samples are placed in tared beakers. The sample weight is noted. If a sample is too big to handle, it is split into parts of approx. 100 g.

Magnets are placed in the beakers and 0.22 M acetate buffer with Tween, EDTA and $PO_4^{3-}$ is added.

The samples are extracted for 60 minutes.

After extraction the samples rest for 30 minutes to allow for the premix to sediment. A 5 ml sample is withdrawn with a pipette. The sample is taken 2-5 cm under the surface of the solution and placed in a centrifuge glass, which is covered by a lid.

The samples are centrifuged for 10 minutes at 4000 rpm.

Analysis

Extracts of feed samples are analyzed directly.

Extracts of premix are diluted to approx. 1.5 FTU/g ($A_{415}$ (main sample)<1.0).

0.22 M acetate buffer with Tween 20 is used for the dilution.

Main Samples

2×100 ml of the supernatant from the extracted and centrifuged samples are placed in marked glass test tubes and a magnet is placed in each tube.

When all samples are ready they are placed on a water bath with stirring. Temperature: 37° C.

3.0 ml substrate is added.

Incubation for exactly 60 minutes after addition of substrate.

The samples are taken off the water bath and 2.0 ml stop solution is added (exactly 60 minutes after addition of substrate).

The samples are stirred for 1 minute or longer.

Feed samples are centrifuged for 10 minutes at 4000 rpm (It is not necessary to centrifuge premix samples).

Blind Samples 100 ml of the supernatant from the extracted and centrifuged samples are placed in marked glass test tubes, and a magnet is placed in each tube.

2.0 ml stop solution is added to the samples.

3.0 ml substrate is added to the samples.

The samples are incubated for 60 minutes at room temperature.

The feed samples are centrifuged for 10 minutes at 4000 rpm (it is not necessary to centrifuge premix samples).

Standards

2×100 ml are taken from each of the 8 standards and also 4×100 ml 0.22 M acetate buffer (reagent blind).

$A_{415}$ is measured on all samples.

Calculation $$\text{FTU/g} = \text{micromol } PO_4^{3-}/(\text{min}*\text{g(sample)})$$

C g sample is weighed out (after grinding).

100 microliters are taken from the extracted and centrifuged sample.

$PO_4^{3-}$ standard curve is linear.

From the regression curve for the $PO_4^{3-}$ standard the actual concentration of the sample is found (concentration in mM):

$$[PO_4^{3-}] = (x-b)/a \quad x = A_{415} \quad a = \text{slope} \quad b = \text{intercept with } y\text{-axis}$$

$$\text{micromol } PO_4^{3-}/\min = \{[PO_4^{3-}](mM) \times \text{Vol}(liter) \times 1000 \text{ micromol/mmol}\}/t$$

t=incubation time in minutes.
Vol=sample volume in liter=0.0001 liter
1000=conversion factor from mmol to micromol $$FTU/g_{prove} = \{(x-b) \times \text{Vol} \times 1000 \times F_p\}/\{a \times t \times C\}$$

C=gram sample weighed out
$F_p$=Relation between the sample taken out and the total sample (after extraction).
Example: 0.100 ml taken from 1000 ml→$F_p$=1000/0.100=10000.
Reduced expression with insertion of the following values:
t=60
Vol=0.0001l
$F_p$=10000

$$FTU/g_{prove} = \{(x-b) \times 0.0001 \times 1000 \times 10000\}/\{a \times 60 \times C\}$$

Example 2

Preparation of a Concentrated Liquid Phytase Preparation

The phytase derived from *Peniophora lycii* is expressed in *Aspergillus oryzae*, fermented and purified, essentially as described in WO 98/28408. The resulting liquid phytase concentrate is a UF (ultra filtration) concentrate of a dry matter content of 18%. The pH is adjusted to 5.

Example 3

Preparation of Phytase Granulates

A coated phytase granulate with 1.5% CSL is prepared as follows:
14.68 kg of a powder composition with the formulation
0.75 kg kaolin, Speswhite, English China Clay
1.80 kg of fibrous cellulose, Arbocel BC 200
11.23 kg finely ground sodium sulphate
0.90 kg Carbohydrate binder, Tackidex G155 from Roquette
is mixed in a Lödige mixer FM 50 and sprayed with 3.15 kg of a spraying liquid consisting of 1.68 kg of water, 0.625 kg of Corn Steep Liquor (Concentrated Corn Steep Liquor (CCSL) supplied by Amylum N.V. with a dry matter content of 48%) and 0.84 kg of Phytase concentrate (18% dry matter content) prepared as described in Example 2. During and after spraying the moist mixture is exposed to a compacting and granulation influence from the multiple set of knives, as described in Example 1 of U.S. Pat. No. 4,106,991.

The percentage of CSL in this as yet un-coated raw granulate is calculated as follows:

$$0.625 \times 0.48/(14.68+0.625 \times 0.48+0.84 \times 0.18) = 0.300/(14.68+0.30+0.672) = 0.300/15.652 = 1.917\% \sim 2\%.$$

The granulate is dried in a fluid bed to a water content below 3%, resulting in a light coloured granulate with the following particle distribution:
10.5%>1100 micro-meter
92.0%>300 micro-m
8.0%<300 micro-m The granulate is finally sifted to get a product with the particle range 300 micro-m to 1100 micro-m, and 6 kg of granulate is coated at 80° C. with 9% fully hydrogenated palm oil, followed by 22.5% of kaolin, Speswhite (dry matter content in 100 g coating material: 22.5 g+9 g=31.5 g), in a manner as described in U.S. Pat. No. 4,106,991, Example 22.

The content of CSL in the resulting final product, the coated granulate, is reduced as compared to the CSL content of the raw granulate as follows: 1.917%/1.315=1.458%~1.5%.

The granulate is sifted to obtain a product with the particle range 300 micro-m to 1200 micro-m.

The control granulate used below is prepared as described above, except for no CSL being added.

Granulates additionally comprising wheat starch and lactose or trehalose are prepared in a corresponding manner.

Example 4

Storage Stability of Phytase Granulates in Premix

The phytase granulates indicated in Table 1 below are prepared according to Example 3. "Control" indicates a phytase granulate prepared according to the method of Example 3, but with no addition of CSL.

The granulates are weighed directly into each vial. The exact weight of the granulate is recorded. The vials are covered with a clean towel and left at room temperature overnight.

The premix ENGA 1-02/Nordkorn. Product. No: 015384 Artikel Nr. 8259 (25 kg drums) is mixed in a Lödige mixer to ensure an even distribution of the premix components and filled into plastic bags with ≈3 kg premix in each bag.

The composition of the premix is as follows (per kilo):

| | | |
|---|---|---|
| 5000000 | IE | Vitamin A |
| 1000000 | IE | Vitamin D3 |
| 13333 | mg | Vitamin E |
| 1000 | mg | Vitamin K3 |
| 750 | mg | Vitamin B1 |
| 2500 | mg | Vitamin B2 |
| 1500 | mg | Vitamin B6 |
| 7666 | mcg | Vitamin B12 |
| 12333 | mg | Niacin |
| 33333 | mcg | Biotin |
| 300 | mg | Folic Acid |
| 3000 | mg | Ca-D-Panthothenate |
| 1666 | mg | Cu |
| 16666 | mg | Fe |
| 16666 | mg | Zn |
| 23333 | mg | Mn |
| 133 | mg | Co |
| 66 | mg | I |
| 66 | mg | Se |
| 5.8% | | Calcium |
| 25% | | Sodium |

50 g±1 g of premix is added to each vial and the vials are closed with a screw-on lid. The premix is added using an adjustable cylindrical "scoop" adjusted to give a volume corresponding to 50 g. The vials are mixed by hand until the granulates are evenly distributed in the premix.

The 0 week samples (closed vials), defining for each granulate the level of 100% activity, are frozen immediately after completion of the sample preparation. The samples which are to be stored at 30° C. are re-opened. The open vials are placed in plastic boxes containing 1 liter of glycerol adjusted with water to 43% rH (62% refractometer dry matter measured on a sugar scale) corresponding to ≈10% water in the samples.

The lids of the plastic boxes are sealed with strong tape. This means that the water activity is 0.43 during the whole test period of 13 weeks.

After completion of the storage period the samples are removed from the glycerol boxes, closed with screw on lids and frozen.

The samples are defrosted in a refrigerator (5° C.) overnight prior to analysis.

The 0 week samples stored at −18° C. and the corresponding samples stored at 30° C. are analysed the same day in order to eliminate day-to-day and person-to-person variation.

The results are shown in Table 1 below; CSL=Corn Steep Liquor and WS=Wheat Starch.

Phytase granulates containing 2% CSL, 3% CSL, and 2% CSL plus 5% WS showed similar performance.

TABLE 1

| Granulate code | Granulate | Percentage residual activity following 13 weeks storage at 30° C. |
|---|---|---|
| 1 | Control granulate | 61% |
| 2 | Control granulate | 64% |
| 3 | 1.5% CSL | 81% |
| 4 | 1.5% CSL | 86% |
| 5 | 1.5% CSL | 84% |
| 6 | 1.5% CSL | 85% |
| 7 | 1.5% CSL + 3.8% WS | 84% |
| 8 | 1.5% CSL + 3.8% WS | 90% |
| 9 | 1.5% CSL + 3.8% WS | 84% |

Example 5

Storage Stability of Phytase Granulates in Feed

The phytase granulates indicated in Table 2 below are prepared according to Example 3. "Control" indicates a phytase granulate prepared according to the usual standard method of Example 3, except for neither WS nor CSL nor disaccharides being added.

The samples of granulates in feed are prepared at Bioteknologisk Institut, Kolding, Denmark.

The composition of the feed is as follows:
74.0% wheat
20.7% roasted soy cake
5.0% soy oil
0.3% Premix Enga 1-02/Nordkorn The feed is dried to a water content of ≤10% water before addition of the phytase granulates.

The granulate batches are mixed into feed and the mixture is pelletized at 65° C.

The feed pellets are sample split and filled into 100 ml sample vials.

The 0 week samples, defining for each granulate the level of 100% activity, are closed with screw on lids and kept at −18° C.

The samples which are to be stored at 30° C. are not closed. The open vials are placed in plastic boxes containing 1 liter of glycerol adjusted with water to 43% rH (62% refractometer dry matter measured on a sugar scale) corresponding to ≈10% water in the samples. The lids of the plastic boxes are sealed with strong tape. This means that the water activity is 0.43 during the whole test period of 13 weeks.

After completion of the storage period the samples are removed from the glycerol boxes, closed with screw on lids and frozen. The samples are defrosted in a refrigerator (5° C.) overnight prior to analysis.

Samples for the homogeneity test are kept refrigerated at +5° C. until analysis.

The mash feed, the feed heated to 65° C., and the feed pellets without added enzyme all contain ≈0.5 FTU/g feed as expected.

5 samples of the mash feed with enzyme added and heated to 65° C. are analysed for homogeneity. The relative standard deviation is 2% to 11%. In conclusion, the homogeneity is acceptable.

5 samples of the feed pellets are analysed for homogeneity. The relative standard deviation is 2% to 10%. In conclusion, the homogeneity is acceptable.

The storage stability is measured after 13 weeks. The 0 week samples stored at −18° C. and the corresponding samples stored at 30° C. are analyzed the same day in order to eliminate day-to-day and person-to-person variation.

The results of the phytase residual activity measurements are shown in Table 2 below (endogenous activity has been subtracted from the total activity before calculating the residual activity); CSL=Corn Steep Liquor and WS=Wheat Starch.

Phytase granulates containing 2% CSL, 3% CSL, and 2% CSL plus 5% WS showed similar performance.

TABLE 2

| Granulate code | Granulate | Percentage residual activity following 13 weeks storage at 30° C. |
|---|---|---|
| 1 | Control granulate | 53% |
| 2 | Control granulate | 55% |
| 3 | 1.5% CSL | 74% |
| 4 | 1.5% CSL | 89% |
| 5 | 1.5% CSL | 82% |
| 6 | 1.5% CSL | 73% |
| 7 | 1.5% CSL + 3.8% WS | 82% |
| 8 | 1.5% CSL + 3.8% WS | 91% |
| 9 | 1.5% CSL + 3.8% WS | 89% |

Example 6

Phytase Granulates Per Se; Granulation Yield and Storage Stability

The liquid concentrate of Example 2 was used to prepare experimental solid phytase compositions according to the method of Example 3.

In a first granulation experiment, the disaccharide lactose was added in an amount of 2% together with 3% of the lactic acid source Corn Steep Liquor (CSL).

In a second granulation experiment, 3% Wheat Starch (WS) was applied—in addition to the two components of the first experiment.

In a third granulation experiment, the disaccharide trehalose, in an amount of 2%, as well as 3% WS, was added together with 3% of the lactic acid source CSL.

The effect on granulation yield and storage stability of the resulting granulates per se is examined.

Granulation yield is calculated as phytase units remaining in the product leaving the granulation unit, relative to phytase units of the liquid concentrate entering the unit.

The storage stability of the resulting phytase granulate composition per se is examined using the following rather strict conditions: 4 weeks, 40° C. and a relative humidity of 60%.

The results are shown in Table 3 below.

TABLE 3

| Experiment | Granulation yield | | Storage stability | |
|---|---|---|---|---|
| | Batch 22 | Batch 24 | Batch 22 | Batch 24 |
| Control | 75% | 70% | 43% | 47% |
| CSL + lactose | 80% | 67% | 47% | 50% |
| CSL + WS + lactose | 81% | 79% | 56% | 54% |
| CSL + WS + trehalose | 85% | 82% | 63% | 62% |

Example 7

Storage Stability of a Granulate Composition of Another Phytase

A liquid phytase concentrate and a solid composition—i.e., a granulate—was prepared according to the teachings of Examples 2 and 3, using a so-called consensus phytase as described in EP 0897010.

Granulation experiments were conducted essentially as described in Example 6. However, for storage stability samples are also stored at 30° C. The results are shown in Table 4 below.

TABLE 4

| | Granulation yield | Storage stability | | |
|---|---|---|---|---|
| | | 30° C. | | 40° C., 60% RH |
| Experiment | | 8 weeks | 17 weeks | 4 weeks |
| Control | 82% | 85% | 85% | 40% |
| CSL + WS + lactose | 92% | 97% | 95% | 48% |

Example 8

Characterization of CSL Using High Performance Liquid Chromatography (HPLC)

15 samples from various batches of CSL from various suppliers (Roquette Freres, 4 Rue Patou, F-59022 Lille Cedex, France; Staral s.a., Z.I.ET Portuaire, B.P. 32, F-67390 Marckolsheim, France; and Cerestar Scandinavia A/S, Skovlytoften 33, DK-2840 Holte, Denmark) are tested as described below.

Carrez-Precipitation

Weigh 5.0 g CSL into a 100 ml flask. Add 40 ml MQ-water (demineralized water filtered through a Milli-q filter) and incubate at 70° C. for 15 minutes while shaking at 200 rpm. Add 12 ml of Carrez-I-solution (Potassium-hexacyanoferrat (II)-tri hydrate) and shake. Add 12 ml Carrez-II-solution (Zinc sulphate-hepta hydrate) and shake. Add 20 ml 0.5N NaOH and shake. Let cool and add MQ-water ad 100 ml, shake. 10 ml of this preparation is transferred to a vial and centrifuged for 10 minutes at 4000 rpm. The supernatant is filtered at a 0.5 micro-m filter for HPLC analysis. Each sample is analyzed twice, include sample blinds (MQ-water and Carrez-solutions).

Chromatography Parameters

Column: Supelcosil LC-18-DB, No. 088877AE
Detector: Shimadzu SPDM6A-diodearray from 220 nm to 350 nm.
Data analysis: For analyzing data, use peak areas resulting from integration at 260 nm.
Pump: HP 1080 gradient pump Eluents: A) MQ-water
B) 30% MeOH
C) 60% MeOH
D) 90% MeOH
Gradients: 0 min A
15 min A
35 min B
50 min C
60 min C
65 min D
70 min D
75 min C
80 min B
85 min A
90 min A The results of variable statistics on 15 samples of CSL analyzed by HPLC are shown in Table 5 below:

TABLE 5

| Peak retention time | Min | Max | Mean | Standard Deviation (SD) | % SD |
|---|---|---|---|---|---|
| 6791 | 22154 | 114227 | 79192 | 25978 | 32.80[7] |
| 7445 | 1934348 | 2326644 | 2135867 | 110911 | 5.19[1] |
| 10331 | 4746 | 132048 | 44503 | 52860 | 118.78 |
| 11844 | 0 | 3020 | 201 | 780 | 387.30 |
| 12440 | 124723 | 183826 | 155946 | 17166 | 11.01[4] |
| 14124 | 79613 | 186731 | 119578 | 35032 | 29.30[6] |
| 15322 | 0 | 27204 | 13205 | 11537 | 87.37 |
| 16187 | 314623 | 380627 | 346898 | 21271 | 6.13[2] |
| 18831 | 18494 | 148325 | 130989 | 10481 | 8.00[3] |
| 26373 | 0 | 8482 | 2288 | 3454 | 150.99 |
| 26833 | 0 | 59860 | 25622 | 19252 | 75.14 |
| 27672 | 0 | 46259 | 24388 | 13200 | 54.12 |
| 28053 | 0 | 11383 | 3085 | 3169 | 102.71 |
| 28762 | 5643 | 60078 | 31762 | 20966 | 66.01 |
| 29491 | 3657 | 14650 | 8970 | 3353 | 37.38[8] |
| 29926 | 40184 | 89538 | 52754 | 14807 | 28.07[5] |
| 30607 | 0 | 44749 | 14732 | 15523 | 105.37 |
| 30951 | 0 | 19732 | 2423 | 5786 | 238.80 |
| 31825 | 0 | 16090 | 2624 | 4909 | 187.06 |
| 32454 | 0 | 15725 | 1288 | 4050 | 314.36 |
| 32636 | 0 | 28268 | 7516 | 9534 | 126.85 |
| 33068 | 0 | 36398 | 4570 | 9707 | 212.42 |
| 33394 | 0 | 96671 | 30197 | 33359 | 110.47 |
| 33646 | 0 | 24856 | 4042 | 7600 | 188.02 |
| 34108 | 0 | 11826 | 2144 | 3922 | 182.94 |
| 34464 | 0 | 29248 | 9794 | 8990 | 91.79 |
| 35309 | 0 | 14392 | 8793 | 6491 | 73.82 |
| 36826 | 0 | 29619 | 9667 | 10423 | 107.82 |
| 42457 | 0 | 45570 | 32023 | 12404 | 38.73[9] |
| 42971 | 29905 | 102074 | 45303 | 18156 | 40.08[10] |
| 43427 | 0 | 49318 | 6293 | 14306 | 227.33 |
| 43812 | 0 | 13837 | 5851 | 4924 | 84.16 |
| 45519 | 0 | 12487 | 3570 | 4815 | 134.87 |
| 46032 | 0 | 11850 | 4728 | 4756 | 100.59 |
| 46654 | 0 | 36357 | 23766 | 11561 | 48.65 |
| 47034 | 0 | 37769 | 17540 | 11212 | 63.92 |
| 47268 | 0 | 20271 | 5414 | 6969 | 128.72 |
| 47784 | 0 | 5218 | 1569 | 2091 | 133.25 |
| 48494 | 0 | 5858 | 1872 | 1595 | 85.20 |
| 48859 | 0 | 10935 | 2923 | 3748 | 128.25 |
| 49180 | 0 | 24091 | 11016 | 8573 | 77.82 |
| 49467 | 0 | 23885 | 10146 | 8372 | 82.52 |
| 49905 | 0 | 22011 | 4205 | 8506 | 202.31 |

In the % SD column of Table 5, characteristic peaks are indicated by way of a superscript number (1, 2, 3, - - -, 9, 10). In what follows, these peaks will be referred to as peak-1, peak-2, peak-3, - - -, peak-9, peak-10, respectively. The whole group of ten peaks is referred to as peaks 1-10. Subgroups are referred to by analogy, e.g., peaks 1-5 for the five peaks numbered 1 to 5, peaks 1, 3, 5 for peak-1, peak-3 and peak-5 etc. Thus, the presence of one or more of these peaks in a sample is indicative of the presence of CSL. In preferred embodiments, the presence of one, two, three, four, five, six, seven, eight, nine or all ten of these peaks is indicative of the presence of CSL. In more preferred embodiments, the presence of five, seven, eight or ten peaks is indicative of the presence of CSL. The presence of five peaks is most preferred.

For samples of an unknown content of CSL, suitable dilutions are found using simple trial-and-error techniques.

The above qualitative method can be made quantitative by comparing with a batch denominated by Roquette Freres to be a standard batch. A particularly preferred standard CSL batch from Roquette Freres is SOLULYS® L 48 L CAS No. 66071-94-1, EINECS: 266-113-4.

The invention claimed is:

1. A solid phytase composition, comprising:
   (a) an enzyme having a phytase activity of above 20 FYT/g of the composition, and
   (b) corn steep liquor in an amount sufficient to stabilize the enzyme having phytase activity, wherein the corn steep liquor is present in an amount of 0.1-15%, and wherein the enzyme having phytase activity in the composition has a residual activity of 73% to 91% following 13 weeks storage at 30° C.

2. The composition of claim 1, having a chromatogram determined by HPLC, which has one or more of peaks 1-10.

3. The composition of claim 1, further comprising a starch material.

4. The composition of claim 1, further comprising wheat starch.

5. The composition of claim 1, further comprising a disaccharide.

6. The composition of claim 1, further comprising a carrier material.

7. The composition of claim 1, further comprising a filler material.

8. The composition of claim 1, further comprising one or more vitamins, one or more minerals or a mixture of both.

9. The composition of claim 1, wherein the phytase activity is at least 25 FYT/g of the composition.

10. The composition of claim 9, wherein the phytase activity is at least 50 FYT/g of the composition.

11. The composition of claim 10, wherein the phytase activity is at least 100 FYT/g of the composition.

12. The composition of claim 11, wherein the phytase activity is at least 250 FYT/g of the composition.

13. The composition of claim 12, wherein the phytase activity is at least 500 FYT/g of the composition.

14. The composition of claim 13, wherein the phytase activity is at least 750 FYT/g of the composition.

15. The composition of claim 14, wherein the phytase activity is at least 1,000 FYT/g of the composition.

16. The composition of claim 1, wherein the phytase activity is in the range of 20-50,000 FYT/g.

17. The composition of claim 1, wherein the phytase activity is in the range of 100-25,000 FYT/g.

18. The composition of claim 1, wherein the phytase activity is in the range of 500-10,000 FYT/g.

19. The composition of claim 1, wherein the phytase activity is in the range of 1,000-5,000 FYT/g.

20. The solid phytase composition of claim 1, wherein corn steep liquor is present in an amount of 0.1-10%.

21. The solid phytase composition of claim 1, wherein corn steep liquor is present in an amount of 1-5%.

22. The solid phytase composition of claim 1, wherein corn steep liquor is present in an amount of about 1.5%.

* * * * *